US009409944B2

(12) United States Patent
Gerwick et al.

(10) Patent No.: US 9,409,944 B2
(45) Date of Patent: Aug. 9, 2016

(54) COMPOSITIONS AND METHODS FOR INHIBITING PROTEASES

(75) Inventors: William H. Gerwick, La Jolla, CA (US); Alban R. Pereira-Badilla, Hayward, CA (US); Tara Byrum, North Charleston, SC (US); Frederick A. Valeriote, Shelby Township, MI (US); Michael Kenneth Gilson, San Diego, CA (US); Andrew T. Fenley, San Diego, CA (US); Bradley S. Moore, La Jolla, CA (US); Andrew Kale, La Jolla, CA (US); Hosana Debonsi, São Paulo (BR)

(73) Assignee: The Regents of the University of California, Oakland, CA (US)

( * ) Notice: Subject to any disclaimer, the term of this patent is extended or adjusted under 35 U.S.C. 154(b) by 58 days.

(21) Appl. No.: 14/131,681

(22) PCT Filed: Jul. 12, 2012

(86) PCT No.: PCT/US2012/046529
§ 371 (c)(1),
(2), (4) Date: May 21, 2014

(87) PCT Pub. No.: WO2013/010018
PCT Pub. Date: Jan. 17, 2013

(65) Prior Publication Data
US 2014/0248333 A1    Sep. 4, 2014

Related U.S. Application Data

(60) Provisional application No. 61/600,387, filed on Feb. 17, 2012, provisional application No. 61/507,507, filed on Jul. 13, 2011.

(51) Int. Cl.
*C07K 5/083* (2006.01)
*A61K 31/336* (2006.01)
*C07K 5/062* (2006.01)

(52) U.S. Cl.
CPC ............ *C07K 5/0808* (2013.01); *A61K 31/336* (2013.01); *C07K 5/06052* (2013.01)

(58) Field of Classification Search
CPC ............... A61K 2300/00; A61K 39/39558; A61K 38/06; A61K 39/3955; A61K 38/05; A61K 38/07
See application file for complete search history.

(56) References Cited

U.S. PATENT DOCUMENTS

| 2005/0222043 A1 | 10/2005 | Stangl et al. |
| 2008/0124286 A1* | 5/2008 | Lisson ................... A61K 8/975 424/61 |
| 2009/0099097 A1 | 4/2009 | Crews et al. |

FOREIGN PATENT DOCUMENTS

| WO | 9628464 A1 | 9/1996 |
| WO | 2007149512 A2 | 12/2007 |
| WO | WO2007/149512 A2 * | 12/2007 ............. A61K 38/05 |

OTHER PUBLICATIONS

Verdoes et al. Mixing of peptides and electrophilic traps gives rise to potent, broad-spectrum proteasome inhibitors. Org. Biomol. Chem., 2007, 5, 1416-1426.*

(Continued)

*Primary Examiner* — Satyanarayana R Gudibande
*Assistant Examiner* — Jia-Hai Lee
(74) *Attorney, Agent, or Firm* — Greer, Burns & Crain, Ltd.; Gregory P. Einhorn (57) ABSTRACT

In particular, in alternative embodiments, the invention provides pharmaceutical compounds and formulations comprising a family of epoxyketone compounds, which include racemic mixtures or racemates, isomers, stereoisomers, diastereoisomers, derivatives and analogs, and methods for making and using them. In alternative embodiments, pharmaceutical compositions and formulations of the invention are administered to an individual in need thereof in an amount sufficient to treat, prevent, reverse and/or ameliorate an infection, disease or condition that can be ameliorated, treated, prevented or reversed by partially or completely inhibiting a chymotrypsin-like protease or a proteasome activity, including e.g., a retroviral infection such as human immunodeficiency virus-1 (HIV-1) infection, an immune disorder, a neurodegenerative disease or condition, or a cancer such as a myeloma or multiple myeloma, an adenocarcinoma such as a lung adenocarcinoma, a pancreatic cancer, a B-cell related cancer, and lymphomas such as non-Hodgkin's lymphoma.

9 Claims, 6 Drawing Sheets

(56) References Cited

OTHER PUBLICATIONS

Kim et al. Proteasome inhibition by the natural products epoxomicin and dihydroeponemycin: insights into specificity and potency. Bioorg Med Chem Lett. Dec. 6, 1999;9(23):3335-40.*

Pereira et al. The Carmaphycins: New Proteasome Inhibitors Exhibiting an α,β-Epoxyketone Warhead from a Marine Cyanobacterium. ChemBioChem 2012, 13: 810-817.*

Svircev et al. Antibacterial, antifungal and cytotoxic activity of terrestrial cyanobacterial strains from Serbia. Sci China Ser C-Life Sci. 2008; 51(10): 941-947.*

Blackburn et al., "Characterization of a new series of non-covalent proteasome inhibitors with exquisite potency and selectivity for the 20S beta5-subunit", The Biochemical Journal, Sep. 15, 2010, 430(3), pp. 461-676.

Bum Soo, Kim, International Search Report and Written Opinion issued in PCT/US2012/046529, Korean Intellectual Property Office, Feb. 28, 2013.

Lindner, Nora, International Preliminary Report on Patentability issued in PCT/US2012/046529, The International Bureau of WIPO, Jan. 14, 2014.

* cited by examiner

Figure 1

Epoxomicin (3)
Actinomycete strain No. Q996-17
J. Antibiotics, 1992, 45, 1746-1752.

n=1, Eponemycin (4)
Streptomyces hygroscopicus
J. Antibiotics, 1990, 43, 8-18.

n=2, Epopromycin A (5)
Streptomyces sp. NK04000
J. Antibiotics, 1997, 50, 261-263.

Epopromycin B (6)
Streptomyces sp. NK04000
J. Antibiotics, 1997, 50, 261-263.

Carfilzomib (7)
Synthetic epoxomicin analogue
Cancer Res 2007, 67, 6383-6391

COMPOSITIONS AND METHODS FOR INHIBITING PROTEASES

CROSS-REFERENCE TO RELATED APPLICATIONS

This United States utility patent application is the §371 national phase of PCT international patent application no. PCT/US2012/046529, having an international filing date of Jul. 12, 2012, which claims benefit of priority to U.S. Provisional Patent Application Ser. No. (USSN) 61/507,507, filed Jul. 13, 2011; and U.S. Ser. No. 61/507,507, filed Feb. 17, 2012. The aforementioned applications are expressly incorporated herein by reference in their entirety and for all purposes.

GOVERNMENT RIGHTS

This invention was made with government support under grants 20091399 (CA100851), and CA127622, awarded by the National Institutes of Health (NIH). The government has certain rights in the invention.

TECHNICAL FIELD

This invention generally relates to drug discovery, medicine and cell biology. In particular, in alternative embodiments, the invention provides pharmaceutical compounds and formulations comprising a family of epoxyketone compounds, which include racemic mixtures or racemates, isomers, stereoisomers, diastereoisomers, derivatives and analogs, and methods for making and using them. In alternative embodiments, pharmaceutical compositions and formulations of the invention are administered to an individual in need thereof in an amount sufficient to treat, prevent, reverse and/or ameliorate an infection, disease or condition that can be ameliorated, treated, prevented or reversed by partially or completely inhibiting a chymotrypsin-like protease or a proteasome activity, including e.g., a retroviral infection such as human immunodeficiency virus-1 (HIV-1) infection, an immune disorder, a neurodegenerative disease, or a cancer such as a myeloma or multiple myeloma, an adenocarcinoma such as a lung adenocarcinoma, a pancreatic cancer, a B-cell related cancer, and lymphomas such as non-Hodgkin's lymphoma.

BACKGROUND

Figure 1:
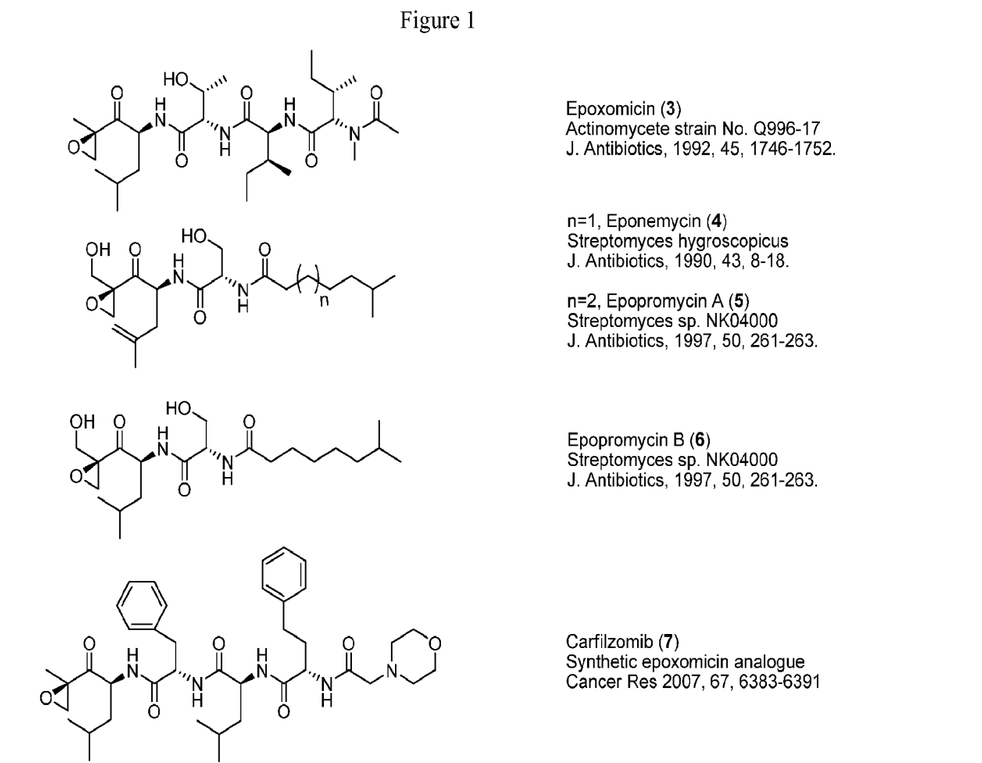
FIG. 1 illustrates structures of epoxomicin (3) and analogues and their synthetic derivatives, including eponemycin (4) and eponemycin A (5), epopromycin B (6) and carfilzomib (7).

Epoxomicin is a naturally occurring, microbial natural product that is a selective proteasome inhibitor with anti-inflammatory activity. Epoxomicin and analogues and their synthetic derivatives are shown in FIG. 1. Carfilzomib (7), a tetrapeptide epoxyketone, is currently in phase HI clinical trials for multiple myeloma.

Figure 2:
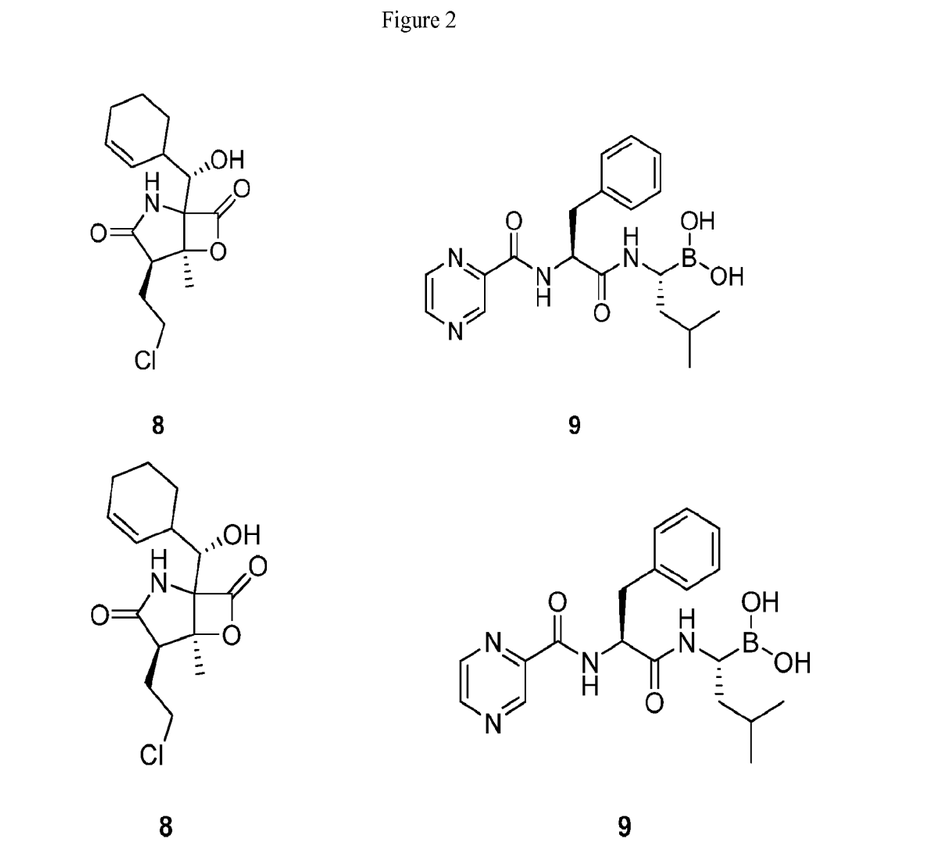
FIG. 2 illustrates structures of proteasome inhibitors including salinoporamide A (8) and bortezomib (9).

Proteasome inhibitors also include structures as shown in FIG. 2, including salinoporamide A (8) and bortezomib (9). Compound 8 is currently in phase I clinical trial for multiple myeloma; compound 9 (marketed as VELCADE™, Millenium Pharmaceuticals) is the first therapeutic proteasome inhibitor to be approved in the U.S. for treating relapsed multiple myeloma and mantle cell lymphoma.

Proteasome inhibitors block the degradation of unneeded or damaged proteins by proteolysis. In addition to anti-cancer activity, proteasome inhibitors have been used to target HIV infection, and have also been shown to have potential in the treatment of autoimmune diseases. For example, proteasome inhibitors have been used to target HIV infection (ritonavir), autoimmune diseases and asthma (lactacystin), and inflammation (epoxomicin).

SUMMARY

In alternative embodiments, the invention provides compositions, pharmaceutical compositions or formulations comprising a compound selected from the group consisting of:

(i) a compound having the formula:

(1)

$X = H, OH, OR, NH_2, NHR, NR_2$ (where $R = Y$)
$Y$ = iso-Propyl, any alkyl, any aryl
$A = O, NH, S$
$B = SH, SCH_3, SOCH_3, (SO_2)CH_3, X$
$n = 1-6$ and alternatively (optionally) X is selected from the group consisting of H, OH, OR, an alkyl group, an alkene group, an aromatic group, $NH_2$, NHR, and $NR_2$,
wherein R is independently selected from the group consisting of an isopropyl group, an alkyl group, an alkene, an aryl group and an aromatic group,
and alternatively (optionally) Y is selected from the group consisting of an isopropyl group, an alkyl group, an alkene, an aryl group and an aromatic group,
and alternatively (optionally) A is selected from the group consisting of O, NH and S,
and alternatively (optionally) Y is selected from the group consisting of O, NH, S, SH, $SCH_3$, $(SO_2)CH_3$, H, OH, OR, an alkyl group, an alkene group, an aromatic group, $NH_2$, NHR, and $NR_2$, wherein R is independently selected from the group consisting of an isopropyl group, an alkyl group, an alkene, an aryl group and an aromatic group,
and alternatively (optionally) B is selected from the group consisting of a lipophilic group, a lipophilic amino acid and an L-methionine derived residue, or
wherein B is selected from the group consisting of S=O (sulfoxide) or $S(=O)_2$ (sulfone), and optionally the S (sulfur atom) has different oxidation states;
or,
(2) a compound having the formula:

wherein R is selected from the group consisting of S=O (sulfoxide) or S(=O)₂ (sulfone), and optionally the S (sulfur atom) has different oxidation states, and alternatively (optionally) the L-methionine derived residue (B) is partially or fully oxidized at the sulfur atom, and alternatively (optionally) the lipophylic substructure (C) is comprised of L-valine and n-hexanoic acid, or equivalents thereof, and alternatively (optionally) B is selected from the group consisting of a lipophilic group, a lipophilic amino acid and an L-methionine derived residue, and alternatively (optionally) A is an epoxiketone substructure, and the L-methionine derived residue B is directly connected to the epoxiketone substructure A, and alternatively (optionally) C comprises a lipophylic fragment, wherein the lipophylic fragment has a two, three, four, five, six, seven or eight or more long carbon chain, and optionally the carbon chain is saturated, or has one or two or more unsaturated (e.g., alkene) moieties;

or, (3) a compound having the formula:

Parent Compound
Carmamycin A

Variations at P1

Variations at P2

-continued or, (4) a compound having the formula:

Parent Compound
Carmaphycin A

Variations at P1

APBIII88A
Chemical Formula: $C_{25}H_{45}N_3O_5S$
Molecular Weight: 499.7069

---

Variations at P2 and truncated analogues

APBIII5223
Chemical Formula: $C_{20}H_{35}N_2O_4$
Molecular Weight: 368.5108

APBIII88B
Chemical Formula: $C_{25}H_{45}N_3O_5S$
Molecular Weight: 499.7069

-continued

APBIII78A1
Chemical Formula: $C_{26}H_{47}N_3O_5$
Molecular Weight: 481.6685

Figure 5:
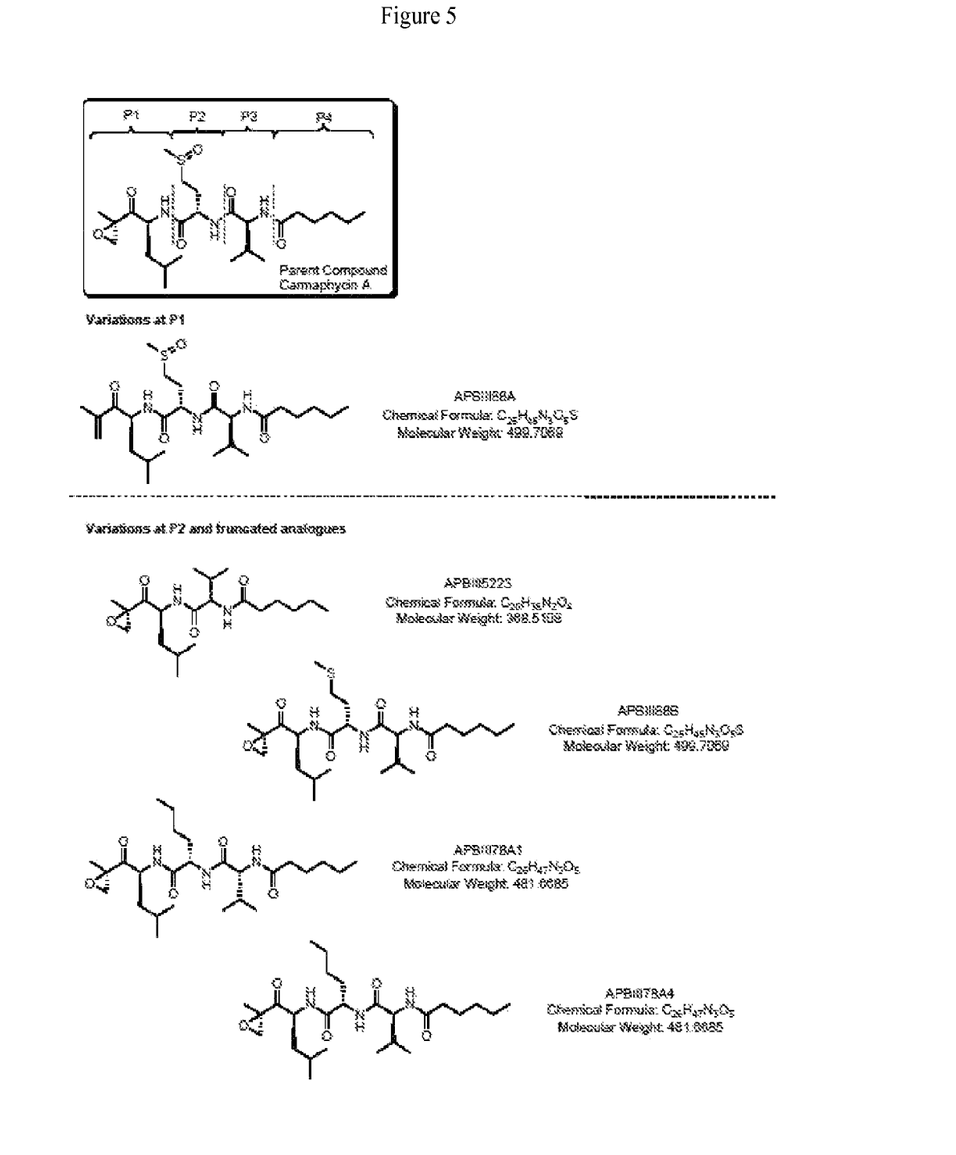
FIG. 5 and FIG. 6 illustrate structures of exemplary compounds of the invention, and the "parent" compounds carmaphycin A and carmamycin A, respectively.
Figure 6:
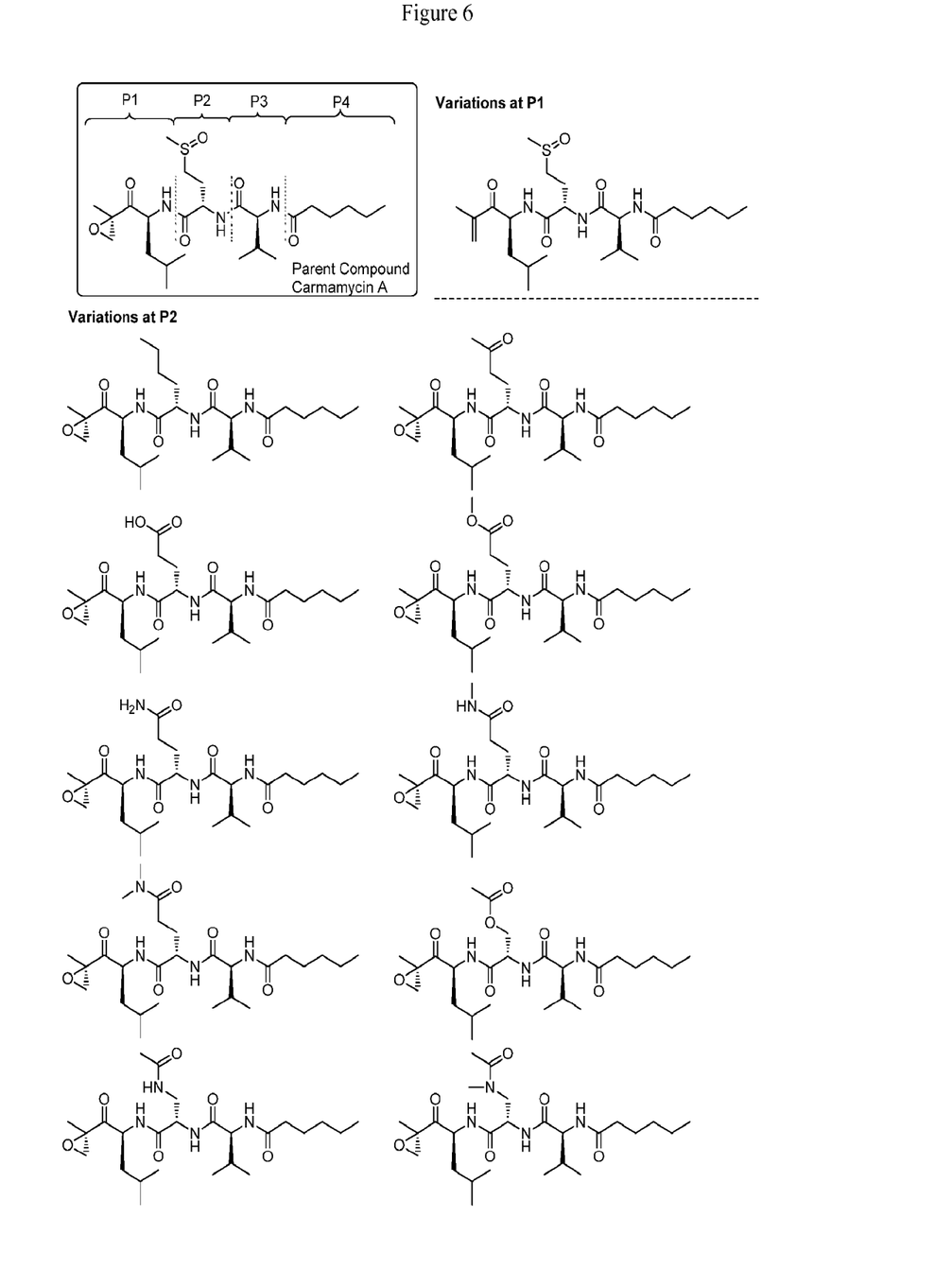

APBIII78A4
Chemical Formula: $C_{26}H_{47}N_3O_5$
Molecular Weight: 481.6685 or,
(5) a compound as set forth in FIG. 5 or FIG. 6;
(ii) a racemic mixture or a racemate, an isomer, a stereoisomer, a diastereoisomer, a bioisostere, a derivative or an analog of a compound of (i);
(iii) the compound of (i) or (ii), wherein any one, several or all of the methyl groups are independently substituted with any alky, alkene, phenoxy or alkoxy group; or, any one, several or all of the methyl groups are independently substituted with a hydrogen, halo, hydroxy (—OH), phenoxy, thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—NO₂), alkoxy, haloalkoxy, thioalkoxy, alkanoyl, haloalkanoyl and/or carbonyloxy group;
(iv) the compound of any of (i) to (iii), wherein any one, several or all of the hydrogen groups are independently substituted with a fluorine or a deuterium;
(v) any combination of any of (i) to (iv), or optionally any one or combination of (i) to (iv) comprising a pharmaceutically acceptable buffer, diluent, stabilizing agent and/or carrier; and
(vi) a pharmaceutically acceptable salt of any of (i) to (v).

In alternative embodiments, the compositions, pharmaceutical compositions or formulations of the invention are formulated as a pharmaceutical composition for enteral or parenteral administration.

In alternative embodiments, the compound has four stereocenters.

In alternative embodiments, the invention provides formulations or pharmaceutical compositions comprising: (a) a compound or composition of the invention; or (b) the formulation or pharmaceutical composition of (a), wherein the compound is formulated for administration in vivo; or for enteral or parenteral administration, or as a tablet, pill, capsule, gel, geltab, liquid, lotion, aerosol or implant.

In alternative embodiments, the invention provides methods for inhibiting a proteasome, or a chymotrypsin-like activity of a 20S proteasome, comprising (a) administering to a cell or contacting a cell with an effective amount of a compound, a composition or a formulation of the invention, or a formulation or a pharmaceutical composition of the invention; or (b) the method of (a), wherein the administration is in vitro, ex vivo or in vivo; or (c) the method of (a) or (b), wherein the cell is a dystrophic or a cancer cell, or an infected cell, or a myeloma cell or multiple myeloma cell, or an adenocarcinoma cell or a lung adenocarcinoma cell, a pancreatic cancer cell, a B-cell related cancer cell, a lymphoma cell or a non-Hodgkin's lymphoma cell.

In alternative embodiments, the invention provides methods for treating, preventing, partially reversing or reversing and/or ameliorating a condition, disease or infection that can be ameliorated, treated, prevented or reversed by partially or completely inhibiting a proteasome activity, comprising:
(a) administering a compound, composition or formulation of the invention, or a formulation or a pharmaceutical composition of the invention, in an amount sufficient to ameliorate, treat, prevent or reverse the disease, condition or infection; or
(b) the method of (a), wherein the administration is to a human or a mammal.

In alternative embodiments, of the methods, the disease, condition or infection is a retroviral infection, a human immunodeficiency virus-1 (HIV-1) infection, an immune disorder or an autoimmune disorder, a cancer, a myeloma or a multiple myeloma, an adenocarcinoma, a lung adenocarcinoma, a pancreatic cancer, a B-cell related cancer, a lymphoma or a non-Hodgkin's lymphoma.

In alternative embodiments, the invention provides methods for causing an accumulation of polyubiquinated proteins in a cell, causing cell cycle arrest, inducing apoptosis and/or inhibiting growth or viability of a tumor cell or a cancer cell or an infected cell, comprising:
(a) administering a compound, composition or formulation of the invention, or a formulation or a pharmaceutical composition of the invention, in an amount sufficient to cause an accumulation of polyubiquinated proteins in the cell, cause cell cycle arrest, induce apoptosis and/or inhibit growth or viability of the tumor cell, cancer cell or infected cell; or
(b) the method of (a), wherein the administration is to a human or a mammal.

In alternative embodiments, of the methods, the cell is a dystrophic or a cancer cell, or an infected cell, or a myeloma cell or multiple myeloma cell, or an adenocarcinoma cell or a lung adenocarcinoma cell, a pancreatic cancer cell, a B-cell related cancer cell, a lymphoma cell or a non-Hodgkin's lymphoma cell.

In alternative embodiments, the invention provides methods for inhibiting a chymotrypsin-like protease, comprising (a) administering to a cell or contacting a cell with an effective amount of a compound, a composition or a formulation of the invention, or a formulation or a pharmaceutical composition of the invention; or (b) the method of (a), wherein the administration is in vitro, ex vivo or in vivo; or (c) the method of (a) or (b), wherein the cell is a nerve cell, a central nervous system (CNS) cell, a cell causative for a neurodegenerative disease, a dystrophic or a cancer cell, or an infected cell, or a myeloma cell or multiple myeloma cell, or an adenocarcinoma cell or a lung adenocarcinoma cell, a pancreatic cancer cell, a B-cell related cancer cell, a lymphoma cell or a non-Hodgkin's lymphoma cell.

In alternative embodiments, the invention provides methods for treating, preventing, partially reversing or reversing and/or ameliorating a condition, disease or infection that can be ameliorated, treated, prevented or reversed by partially or completely inhibiting activity of a chymotrypsin-like protease, comprising:

(a) administering a compound, composition or formulation of the invention, or a formulation or a pharmaceutical composition of the invention, in an amount sufficient to ameliorate, treat, prevent or reverse the disease, condition or infection;

(b) the method of (a), wherein the administration is to a human or a mammal; or (c) the method of (a) or (b), wherein the condition, disease or infection is a neurodegenerative disease or condition, or a condition, disease or infection having a neurodegenerative component, which optionally is Amyotrophic lateral sclerosis (ALS/Lou Gehrig's Disease), Parkinson disease, Huntington's disease or Alzheimer's disease.

In alternative embodiments, the invention provides kits comprising a compound, composition or formulation of the invention, or a formulation or a pharmaceutical composition of the invention, and optionally comprising instructions on practicing a method of the invention.

In alternative embodiments, the invention provides nanoparticles, nanolipoparticles, vesicles or liposomal membranes comprising a compound, composition or formulation of the invention, or a formulation or a pharmaceutical composition of the invention.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides pharmaceutical compounds and formulations comprising a family of epoxyketone compounds, which include racemic mixtures or racemates, isomers, stereoisomers, diastereoisomers, derivatives and analogs, and methods for making and using them. In alternative embodiments, pharmaceutical compositions and formulations of the invention are administered to an individual in need thereof in an amount sufficient to treat, prevent, reverse and/or ameliorate an infection, disease or condition that can be ameliorated, treated, prevented or reversed by partially or completely inhibiting a chymotrypsin-like protease or a proteasome activity, including e.g., a retroviral infection such as human immunodeficiency virus-1 (HIV-1) infection, an immune disorder, a neurodegenerative disease or condition, or a cancer such as a myeloma or multiple myeloma, an adenocarcinoma such as a lung adenocarcinoma, a pancreatic cancer, a B-cell related cancer, and lymphomas such as non-Hodgkin's lymphoma.

In one embodiment, epoxyketone compounds of the invention represent a new class of secondary metabolites produced by an assemblage of marine cyanobacteria, tentatively identified as *Schizothrix* sp. The cyanobacterial consortium was collected while snorkeling south of Carmabi beach, Curaçao. Presumably from a mixed peptide-polyketide biogenetic origin, in alternative embodiments structures of these metabolites, and compounds of this invention, feature:

(i) A reactive epoxiketone substructure (A), responsible for its bioactivity, and likely derived from the amino acid L-leucine which has been extended by one acetate unit and one S-adenosyl methionine (SAM)-derived methyl group.

(ii) An L-methionine derived residue (B), partially or fully oxidized at the sulfur atom, and suspected to serve as a hydrogen bond acceptor.

(iii) A simple lipophylic substructure (C) comprised of L-valine and n-hexanoic acid.

Exemplary Compound 1 encompasses (comprises) a total of five stereocenters. In alternative embodiments, the chiral center comprised by the sulfoxide functional moiety is racemic, making this material an actual 1:1 mixture of two diastereoisomers.

In alternative embodiments, exemplary compound 2 possesses four stereocenters.

Total synthesis was used to determine their relative and absolute configurations, as well as to provide material necessary for bioactivity assays, since they were initially isolated in meager quantities from their natural source (1, 1.7 mg; 2, 0.053 mg). Both exemplary compounds of the invention 1 and 2 proved to be readily accessible via organic synthesis, with unoptimized overall yields of 10 and 7% for 1 and 2, respectively.

A third exemplary compound of the invention consists of a distinct epoxyketone residue sharing substructures B and C with metabolite/compound 1, as determined by HRESI MS/MS experiments. Only 0.016 mg of material was initially obtained. HRESIMS indicated the molecular formula $C_{27}H_{49}N_3O_7S$, is consistent with a difference of two $CH_2$ groups and one oxygen atom in comparison with exemplary compound 1.

The presence of an L-methionine derived residue B directly connected to the epoxiketone substructure A is completely unprecedented. Also novel are the different oxidation states exhibited by the sulfur atom in that same residue, which confers to this side arm hydrogen bonding capabilities. Finally, the two building blocks comprising the lipophylic fragment C are also unique.

Noting that the invention is not limited by any particular mechanism of action, we demonstrated that compounds of the invention can act as proteasome inhibitors, e.g., can block or inhibit the action of proteasomes, which are large protein complexes located in the cellular nucleus and cytoplasm that degrade unneeded or damaged proteins by proteolysis (the hydrolytic breaking of peptide bonds). In alternative embodiments, compounds of the invention are effective anticancer agents, can be used to treat retroviral inventions such as HIV infection, and can treatment or ameliorate autoimmune diseases. Although proteasome inhibitors possess effective anticancer activity, have been used to target HIV infection, and have also been shown to have potential in the treatment of autoimmune diseases, the scope of activity or effectiveness of compounds of this invention are not limited by any particular mechanism of action.

Noting that the invention is not limited by any particular mechanism of action, compounds of the invention can act as (partial or complete) proteasome inhibitors; can irreversibly bind to and inhibit the chymotrypsin-like activity of the 20S proteasome; can cause an accumulation of polyubiquinated proteins; can cause cell cycle arrest; can induce apoptosis; and/or can inhibit of tumor or cancer cell growth.

We discovered the new natural products, compounds having formulas 1 and 2, from a collection of marine cyanobacteria obtained from Curaçao in the Netherland Antilles. We were led to isolate this compound from cancer cell toxicity of the extract and semi-purified fractions. Further biological testing of pure compound 1 showed that it inhibited the beta 5 subunit (chymotrypsin-like) of the *Saccharomyces cerevisiae* 20S proteasome with an $IC_{50}$ of 5.3±0.5 nM, only slightly less potent than salinosporamide A ($IC_{50}$ of 1.4±0.2 nM), currently in phase I clinical trials for the treatment of multiple myeloma. The compound also showed high cytotoxicity to human lung adenocarcinoma (H460) cells with an $EC_{50}$ of 14.5 nM.

Products of Manufacture, Kits

The invention also provides products of manufacture, kits and pharmaceuticals for practicing the methods of this invention. In alternative embodiments, the invention provides products of manufacture, kits and/or pharmaceuticals comprising all the components needed to practice a method of the invention.

Formulations and Pharmaceutical Compositions

In alternative embodiments, the invention provides pharmaceutical formulations or compositions for use in in vivo, in vitro or ex vivo methods to treat, prevent, reverse and/or ameliorate an infection, disease or condition that can be ameliorated, treated, prevented or reversed by partially or completely inhibiting proteasome activity, including e.g., a retroviral infection such as human immunodeficiency virus-1 (HIV-1) infection, an immune disorder or a cancer such as a myeloma or multiple myeloma, an adenocarcinoma such as a lung adenocarcinoma, a pancreatic cancer, a B-cell related cancer, and lymphomas such as non-Hodgkin's lymphoma.

In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compositions (which include racemic mixtures or racemates, isomers, stereoisomers, derivatives and/or analogs of compounds of the invention) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. By using liposomes, particularly where the liposome surface carries ligarids specific for target cells (e.g., an injured or diseased neuronal cell or CNS tissue), or are otherwise preferentially directed to a specific tissue or organ type, one can focus the delivery of the active agent into a target cells in an in vivo, in vitro or ex vivo application.

Nanoparticles, Nanolipoparticles and Liposomes

The invention also provides nanoparticles, nanolipoparticles, vesicles and liposomal membranes comprising compounds used to practice the methods of this invention, e.g., to deliver compositions of the invention (which include racemic mixtures or racemates, isomers, stereoisomers, derivatives and/or analogs of compounds of the invention) to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a dendritic cell, or an injured or disease CNS tissue, and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent (e.g., apratoxin F and apratoxin G compounds, and/or apratoxin F and apratoxin G derivatives and/or analogs thereof), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (which include racemic mixtures or racemates, isomers, stereoisomers, derivatives and/or analogs of compounds of the invention) used to practice this invention to a desired cell type (e.g., a dendritic cell, or any CNS tissue in need thereof), as described e.g., in U.S. Pat. Pub. No. 20070110798.

The invention also provides nanoparticles comprising compounds (which include racemic mixtures or racemates, isomers, stereoisomers, derivatives and/or analogs of compounds of the invention) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention (which include racemic mixtures or racemates, isomers, stereoisomers, derivatives and/or analogs of compounds of the invention) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations of the invention can be administered for prophylactic and/or therapeutic treatments. In therapeutic applications, compositions are administered to a subject already suffering from a disease, condition, infection or defect in an amount sufficient to cure, alleviate or partially arrest the clinical manifestations of the disease, condition, infection or disease and its complications (a "therapeutically effective amount"). For example, in alternative embodiments, pharmaceutical compositions and formulations of the invention are administered to an individual in need thereof in an amount sufficient to treat, prevent, reverse and/or ameliorate an infection, disease or condition that can be ameliorated, treated, prevented or reversed by partially or completely inhibiting proteasome activity, including e.g., a retroviral infection such as human immunodeficiency virus-1 (HIV-1) infection, an immune disorder or a cancer such as a myeloma or multiple myeloma, an adenocarcinoma such as a lung adenocarcinoma, a pancreatic cancer, a B-cell related cancer, and lymphomas such as non-Hodgkin's lymphoma.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for oral administration of compositions used to practice the invention are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating any neurological or neuromuscular disease, condition, infection or injury, including related inflammatory and autoimmune diseases and conditions, and the like. For example, the methods and/or compositions and formulations of the invention can be co-formulated with and/or co-administered with, fluids, antibiotics, cytokines, immunoregulatory agents, anti-inflammatory agents, pain alleviating compounds, complement activating agents, such as peptides or proteins comprising collagen-like domains or fibrinogen-like domains (e.g., a ficolin), carbohydrate-binding domains, and the like and combinations thereof.

Bioisosteres of Compounds of the Invention

In alternative embodiment, the invention also provides bioisosteres of compounds of the invention. Bioisosteres of the invention are compounds of the invention comprising one or more substituent and/or group replacements with a substituent and/or group having substantially similar physical or chemical properties which produce substantially similar biological properties to compounds of the invention. In one embodiment, the purpose of exchanging one bioisostere for another is to enhance the desired biological or physical properties of a compound without making significant changes in chemical structures.

For example, in one embodiment, one or more hydrogen atom(s) is replaced with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

The invention will be further described with reference to the examples described herein; however, it is to be understood that the invention is not limited to such examples.

EXAMPLES

Example 1

Exemplary Compounds and Methods of Making them

This example describes exemplary protocols for making compounds of the invention.

While the invention is not limited by any particular mechanism of action, in one embodiment, compounds of the invention can work in a way (have a mechanism of action) analogous to epoxomicin and its analogues, which have been found to irreversibly bind to and inhibit the chymotrypsin-like activity of the 20S proteasome, an enzyme responsible for degrading a large variety of cellular proteins. Inhibition of proteasome-mediated proteolysis results in an accumulation of polyubiquinated proteins; cause cell cycle arrest; induce apoptosis; and/or inhibit cancer cell or tumor growth.

Figure 3:
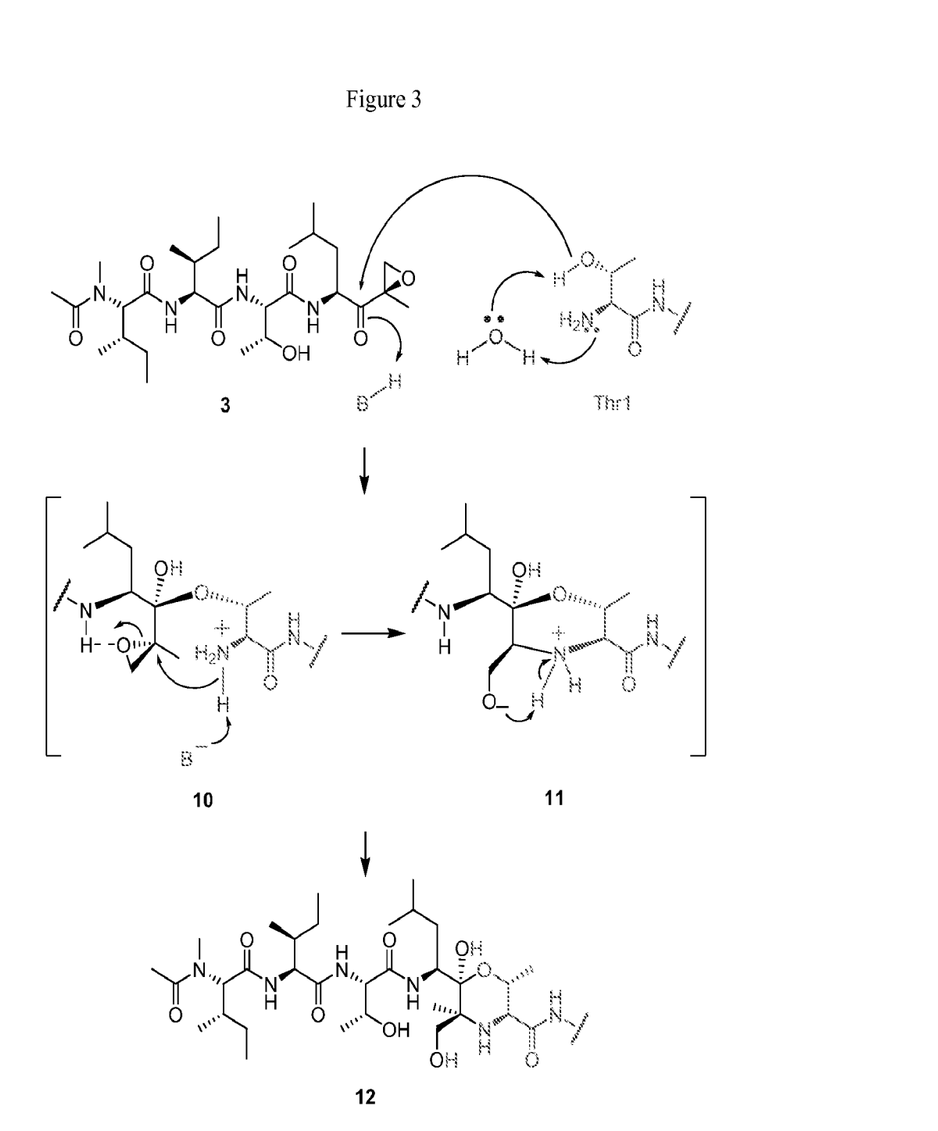
FIG. 3 schematically illustrates the formation of a morpholino adduct (compound 12) between an epoxyketone pharmacophore and the active site amino terminal Thr1 of the β5 subunit of a S. cerevisiae 20S proteasome complex.

Referring to FIG. 3: according to the crystal structure of the epoxomicin (compound 3): S. cerevisiae 20S proteasome complex, the formation of a morpholino adduct (compound 12) takes place between the epoxyketone pharmacophore and the active site amino terminal Thr1 of the β5 subunit. Nucleophilic attack by Thr1 on epoxomicin results in hemiacetal formation (intermediate compound 10) followed by subsequent cyclization of Thr1 α-nitrogen onto the epoxide resulting in an inversion of C2 and formation of the morpholino adduct (intermediate compound 11). Candidate residues for H-B and B- are the Thr1 amino terminus, a bound water molecule, and the invariant Ser129 residue.

Figure 4:
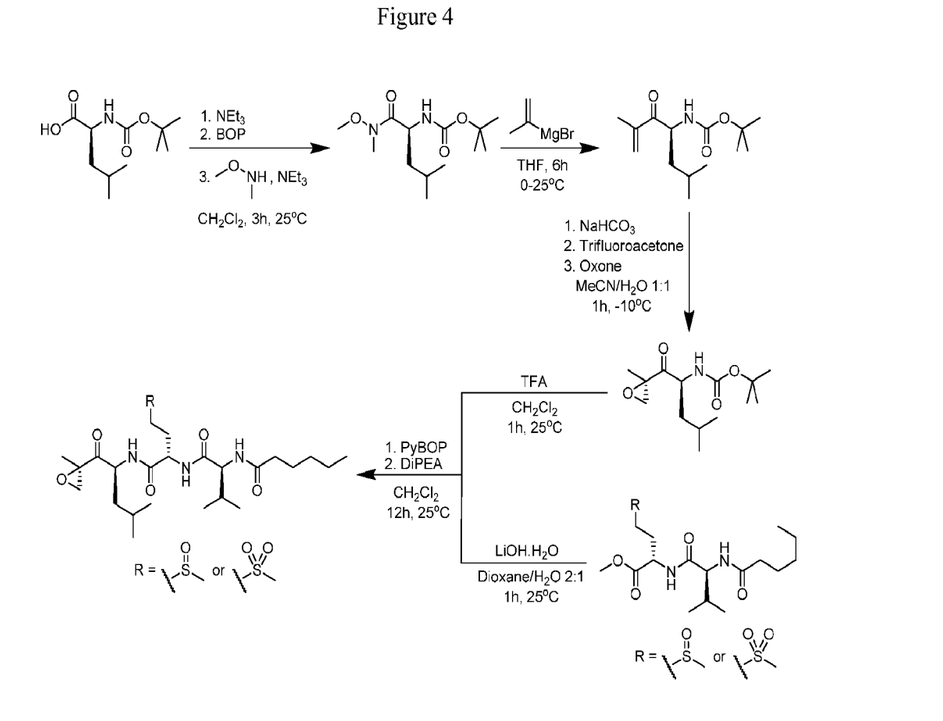
FIG. 4 schematically illustrates an exemplary scheme to synthesize compounds of the invention.

Structures of exemplary compounds of the invention have been elucidated by means of NMR and HRESIMS data. Their absolute and relative configurations were determined by total synthesis, as illustrated in FIG. 4, which at the same time produced material available for further biological testing, thus enabling a constant supply of both compounds. FIG. 4 illustrates a schematic of an exemplary scheme to synthesize compounds of the invention.

A number of embodiments of the invention have been described. Nevertheless, it will be understood that various modifications may be made without departing from the spirit and scope of the invention. Accordingly, other embodiments are within the scope of the following claims.

What is claimed is:

1. A composition, a pharmaceutical composition or a formulation comprising a compound selected from the group consisting of:

(i) a compound having the formula:

n = 1-6 wherein X is selected from the group consisting of H, OH, OR, an alkyl group, an alkene group, an aromatic group, $NH_2$, NHR, and $NR_2$, wherein R is independently selected from the group consisting of an isopropyl group, an alkyl group, an alkene, an aryl group and an aromatic group, wherein A is selected from the group consisting of O, NH and S, wherein Y is selected from the group consisting of O, NH, S, SH, $SCH_3$, $(SO_2)CH_3$, H, OH, OR, an alkyl group, an alkene group, an isopropyl group, an aryl group, an aromatic group, $NH_2$, NHR, and $NR_2$, wherein R is independently selected from the group consisting of an isopropyl group, an alkyl group, an alkene, an aryl group and an aromatic group, wherein B is selected from the group consisting of S=O (sulfoxide) or S(=O)₂ (sulfone), and optionally the S (sulfur atom) has different oxidation states (ii) a racemic mixture or a racemate, an isomer, a stereoisomer, a diastereoisomer, of a compound of (i);

(iii) the compound of (i) or (ii), wherein any one, several or all of the methyl groups are independently substituted with any alky, alkene, phenoxy or alkoxy group; or, any one, several or all of the methyl groups are independently substituted with a hydrogen, halo, hydroxy (—OH), phenoxy, thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—NO₂), alkoxy, haloalkoxy, thioalkoxy, alkanoyl, haloalkanoyl and/or carbonyloxy group;

(iv) the compound of any of (i) to (iii), wherein any one, several or all of the hydrogen groups are independently substituted with a fluorine or a deuterium;

(v) any combination of any of (i) to (iv), or optionally any one or combination of (i) to (iv) comprising a pharmaceutically acceptable buffer, diluent, stabilizing agent and/or carrier; and (vi) a pharmaceutically acceptable salt of any of (i) to (v).

2. The compound of claim 1, formulated as a pharmaceutical composition for enteral or parenteral administration.

3. The compound of claim 1, wherein the compound has four stereocenters.

4. A formulation or a pharmaceutical composition comprising a compound or composition of claim 1.

5. The formulation or a pharmaceutical composition of claim 4, wherein the compound is formulated for administration in vivo; or for enteral or parenteral administration, or as a tablet, pill, capsule, gel, geltab, liquid, lotion, aerosol or implant.

6. The compound of claim 1, wherein the compound has the formula:

wherein R is selected from the group consisting of S=O (sulfoxide) or S(=O)₂ (sulfone), and optionally the S (sulfur atom) has different oxidation states.

7. The compound of claim 1, wherein any one, several or all of the methyl groups are independently substituted with any alky, alkene, phenoxy or alkoxy group.

8. The compound of claim 1, wherein any one, several or all of the methyl groups are independently substituted with a hydrogen, a halo, a hydroxy (—OH), a phenoxy, thiol (—SH), a cyano (—CN), a formyl (—CHO), an alkyl, a haloalkyl, an alkene, an alkenyl, an alkynyl, a heteroalkyl, a heteroalkenyl, a heteroalkynyl, an aryl, a substituted aryl, an amino, a nitro (—NO₂), an alkoxy, a haloalkoxy, a thioalkoxy, an alkanoyl, a haloalkanoyl and/or a carbonyloxy group.

9. The compound of claim 1, wherein any one, several or all of the hydrogen groups are independently substituted with a fluorine or a deuterium.

* * * * *